United States Patent
Meswania (10) Patent No.: US 7,044,976 B2
(45) Date of Patent: May 16, 2006

(54) PROSTHESIS FOR LONG BONE REPLACEMENT IN HUMANS AND ANIMALS

(75) Inventor: Jay Meswania, St. Albans (GB)

(73) Assignee: Stanmore Implants Worldwide, Ltd. (GB)

( * ) Notice: Subject to any disclaimer, the term of this patent is extended or adjusted under 35 U.S.C. 154(b) by 213 days.

(21) Appl. No.: 10/450,559

(22) PCT Filed: Dec. 7, 2001

(86) PCT No.: PCT/GB01/05456

§ 371 (c)(1),
(2), (4) Date: Jun. 12, 2003

(87) PCT Pub. No.: WO02/47585

PCT Pub. Date: Jun. 20, 2002

(65) Prior Publication Data

US 2004/0054420 A1    Mar. 18, 2004

(30) Foreign Application Priority Data

Dec. 15, 2000  (GB) .................................. 0030643

(51) Int. Cl.
*A61F 2/32*    (2006.01)

(52) U.S. Cl. ................ 623/22.45; 623/23.44; 623/22.42

(58) Field of Classification Search .......... 623/22.45, 623/22.42, 22.46, 22.44, 22.43, 22.41, 23.18, 623/23.21, 23.26, 23.44, 20.15, 20.34, 20.36
See application file for complete search history.

(56) References Cited

U.S. PATENT DOCUMENTS

| | | | | | |
|---|---|---|---|---|---|
| 4,623,349 | A | * | 11/1986 | Lord ........................ | 623/23.44 |
| 4,946,379 | A | * | 8/1990 | Berchem ................... | 623/23.44 |
| 4,963,155 | A | * | 10/1990 | Lazzeri et al. ........... | 623/22.42 |
| 6,048,365 | A | * | 4/2000 | Burrows et al. .......... | 623/23.15 |
| 6,613,092 | B1 | * | 9/2003 | Kana et al. .............. | 623/20.15 |

* cited by examiner

*Primary Examiner*—Pedro Philogene
(74) *Attorney, Agent, or Firm*—Galgano & Burke, LLP (57) ABSTRACT

A modular system for the formation of a prosthesis for the replacement of a long bone in a human or animal body. The system provides a prosthesis having a proximal or distal end component such as a trochanter or condylar head, forming one component of a prosthetic joint, a shaft for assembly with a distal or proximal end component and a stem for engagement in a resected bone. The systems allows the assembly of a custom fitted prosthesis for a limited range of components.

14 Claims, 8 Drawing Sheets

PROSTHESIS FOR LONG BONE REPLACEMENT IN HUMANS AND ANIMALS

This invention relates to prostheses for partial or total replacement of a long bone in human or animal bodies.

In the case where limbs are badly damaged or large amounts of bone must be surgically removed, e.g., in the case of treatment of bone cancer, there is a need for prostheses which replace a large part of the natural bone and which can be assembled by the surgeon to meet a wide range of conditions. The present invention provides a modular system for constructing effectively customised prostheses to meet a range of such surgical requirements. Typical requirements may be, for example, to replace the proximal or distal femur or perhaps the total replacement of the femur.

According to one aspect of the present invention there is provided a prosthesis for partial or total replacement of a long bone in humans or animals, said prosthesis comprising a proximal or distal end component forming one component of a prosthetic joint, a shaft assembled with the distal or proximal end and a stem for engagement in a resected bone, the shaft, stem and the distal or proximal end components being connected by male and female tapers, each male taper including a projection which extends longitudinally of the prosthesis but is offset from its axis and engages in a corresponding recess in the female taper, a crosshole being provided for access transversely to the region of the end of the male taper by a disassembly tool, and wherein said projection maintains adjacent components in the desired angular relationship.

The invention also includes other features including a collar which may be assembled to the shaft or extension thereof, the collar being dimensioned to abut the resected face of bone into which the prosthesis is to be fitted, the collar having a portion adapted to taper towards the resected face and having a surface treatment designed to encourage bone growth over the tapered surface of the collar.

In the case of proximal femoral replacement prostheses, the prosthesis preferably includes a trochanter replacement component assembled with a shaft and stem, the trochanter replacement component being shaped to correspond approximately with an anatomical trochanter and including a femoral neck for receiving a femoral ball and a generally flat face opposite the femoral neck for connection to residual bone or soft tissue.

Detailed features of prostheses in accordance with the invention will become apparent from the accompanying drawings, in which.

Figure 1:
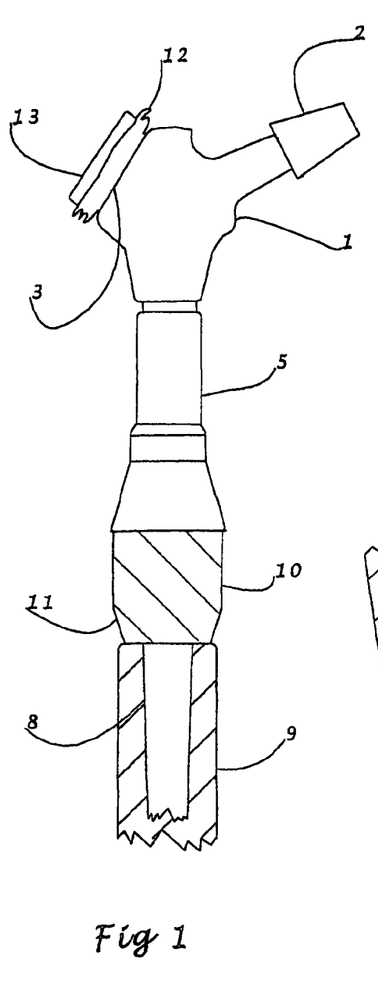
FIG. 1 is a side elevation of assembled components of a proximal femoral prosthesis.

Referring first to FIG. 1, this drawing shows diagrammatically an assembled, proximal femoral prosthesis comprising a trochanter component 1 having a femoral neck 2, which is tapered to receive a femoral ball in a conventional fashion. The trochanter component is shown in more detail in the views shown in FIGS. 3A and 3B and it may be seen that it corresponds roughly to the anatomical shape and has a generally flat face 3 for attachment to any residual bone or to soft tissues. The trochanter component 1 has an internal female taper, best seen in FIG. 3A and is assembled onto a male taper carried by a shaft 5. The detailed construction of shaft 5 are apparent from the views in FIG. 4A and it will be seen that shaft 5 has a male taper 33 at one end for engagement into the female taper of the trochanter component 1 and its other end has a female taper 7 for engagement with one end of a stem 8 (shown in more detail in FIG. 5).

Figure 6:
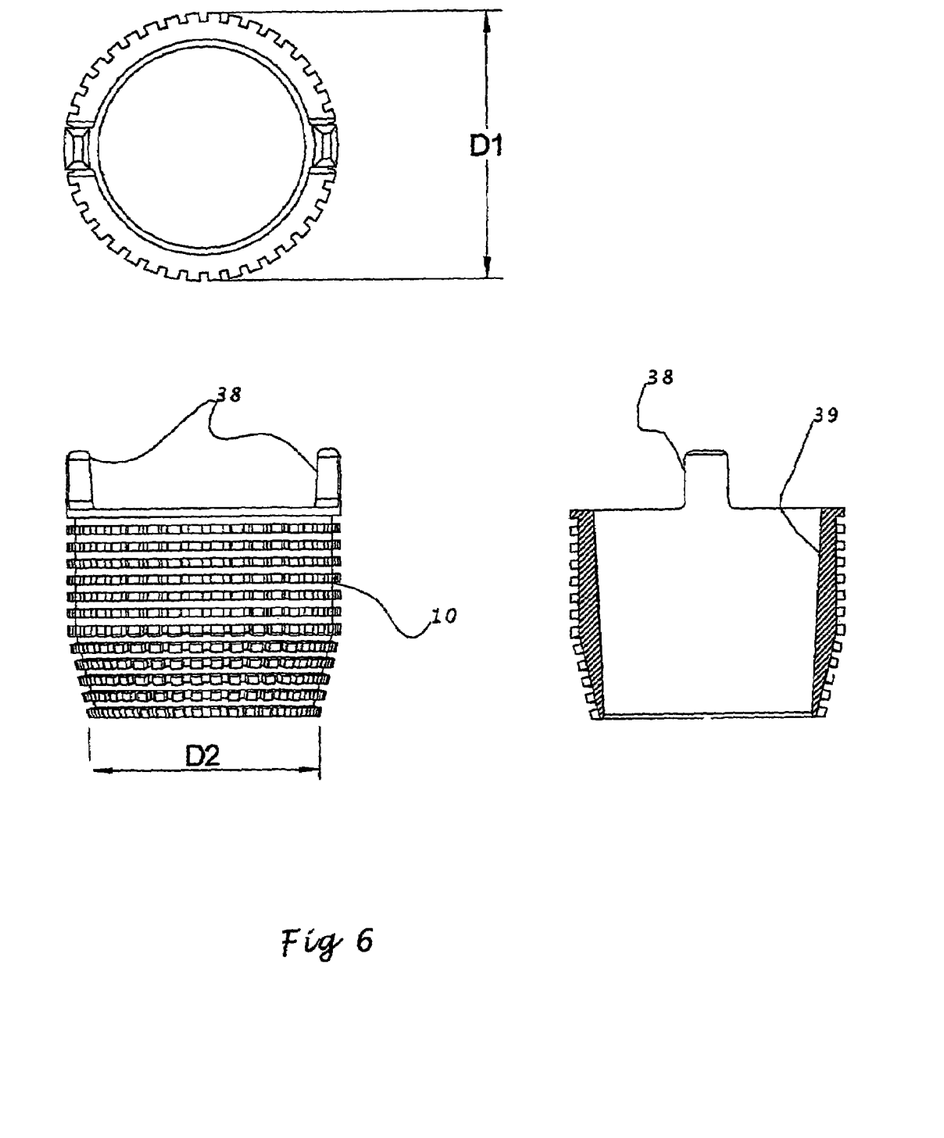
FIG. 6 shows various views of a collar for use in the prosthesis in accordance with the invention and FIG. 7 shows several views of a modular extension shaft for use in the present invention.

Stem 8 is fitted into a resected femur 9 either by press-fit or by using bone cement. Surrounding the distal end of the shaft 5, is a collar 10 which is shown in more detail in FIG. 6. Collar 10 has a distal lower end 11 which abuts cancellous bone forming the face of resected bone 9. The dimensions of collar 10 are selected so that the end face of collar 10 terminates in board of the external dimension of the bone 9. Collar 10 is formed on its external surface with stipples or a bone growth stimulating material such as hydroxyapatite. These measures encourage cancellous bone to grow over the surface of collar 10 and help to more firmly lock the prosthesis into the residual resected bone 9.

It is often possible when removing damaged bone or tumour to retain the residual portion 12 of the trochanter. This residual piece of bone may have ligaments or other soft tissue attached to it and it is useful to use this to assist in stabilising the trochanter replacement component. The residual bone 12 can be attached to the trochanter component by clamping a plate 13 to the face 3 of the trochanter component.

Figure 2:
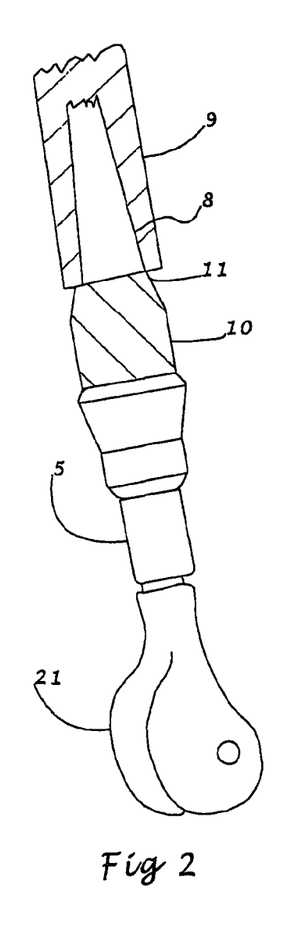
FIG. 2 is a side elevation of a distal femoral prosthesis in accordance with the invention.

FIG. 2 shows a view of an assembled distal prosthesis comprising a condylar head component 21 forming one part of the knee joint which is connected to a shaft 5 in an analogous way to the way in which the trochanter component 1 is connected to the shaft 5 in FIG. 1. Similarly, shaft 5 is connected to stem 8 in a similar way to that previously described in connection with FIG. 1 and collar 10 is slid over the tapered lower portion of shaft member 5 just as described above in connection with FIG. 1 and has a distal tapered portion 11 which abuts the resected fac of the femur 9. In a similar way, this encourages bone growth over the surface of the collar 10.

Figure 3A:
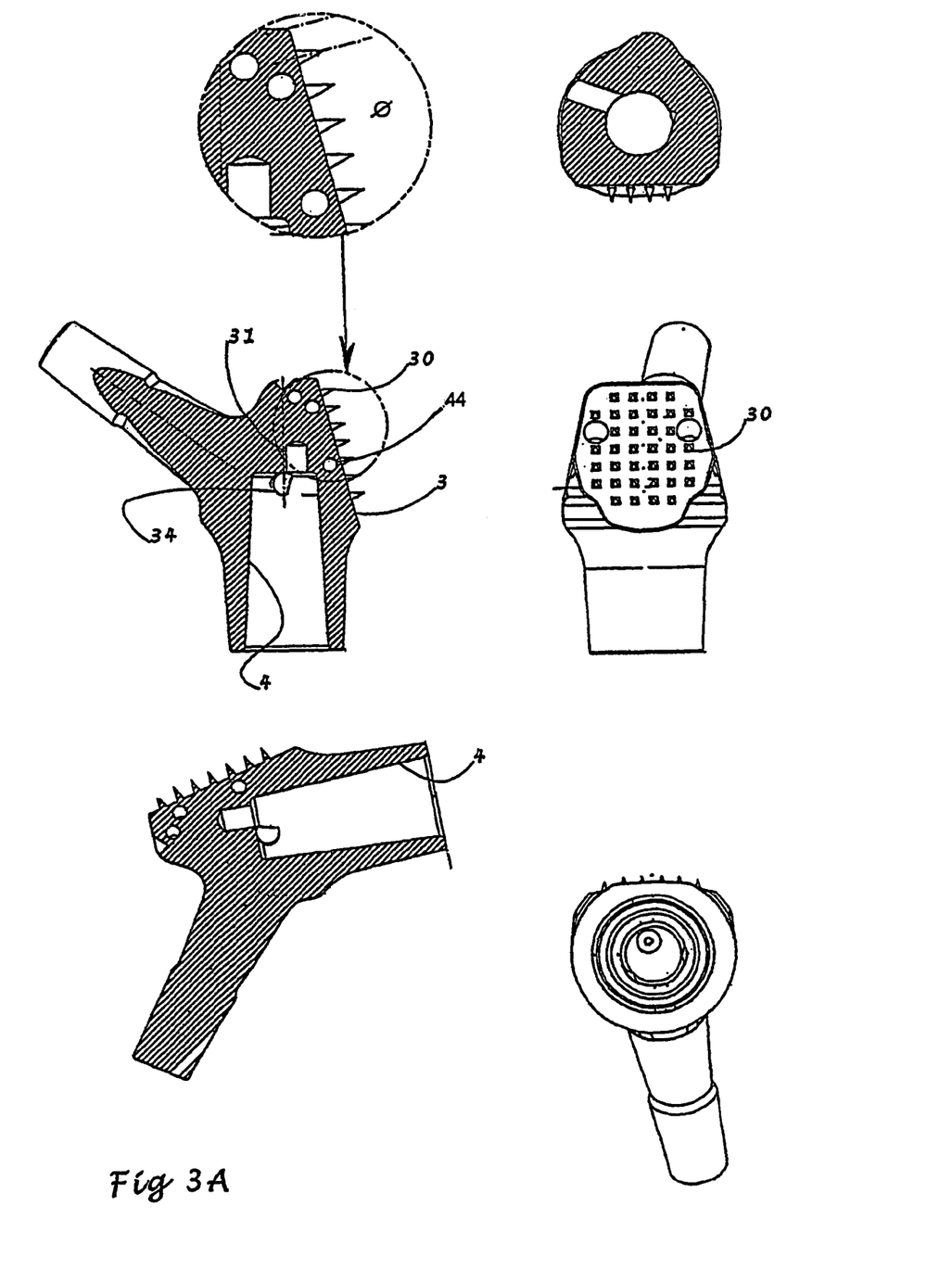
FIG. 3A shows various views of a trochanter replacement component in accordance with the invention.
Figure 3B:
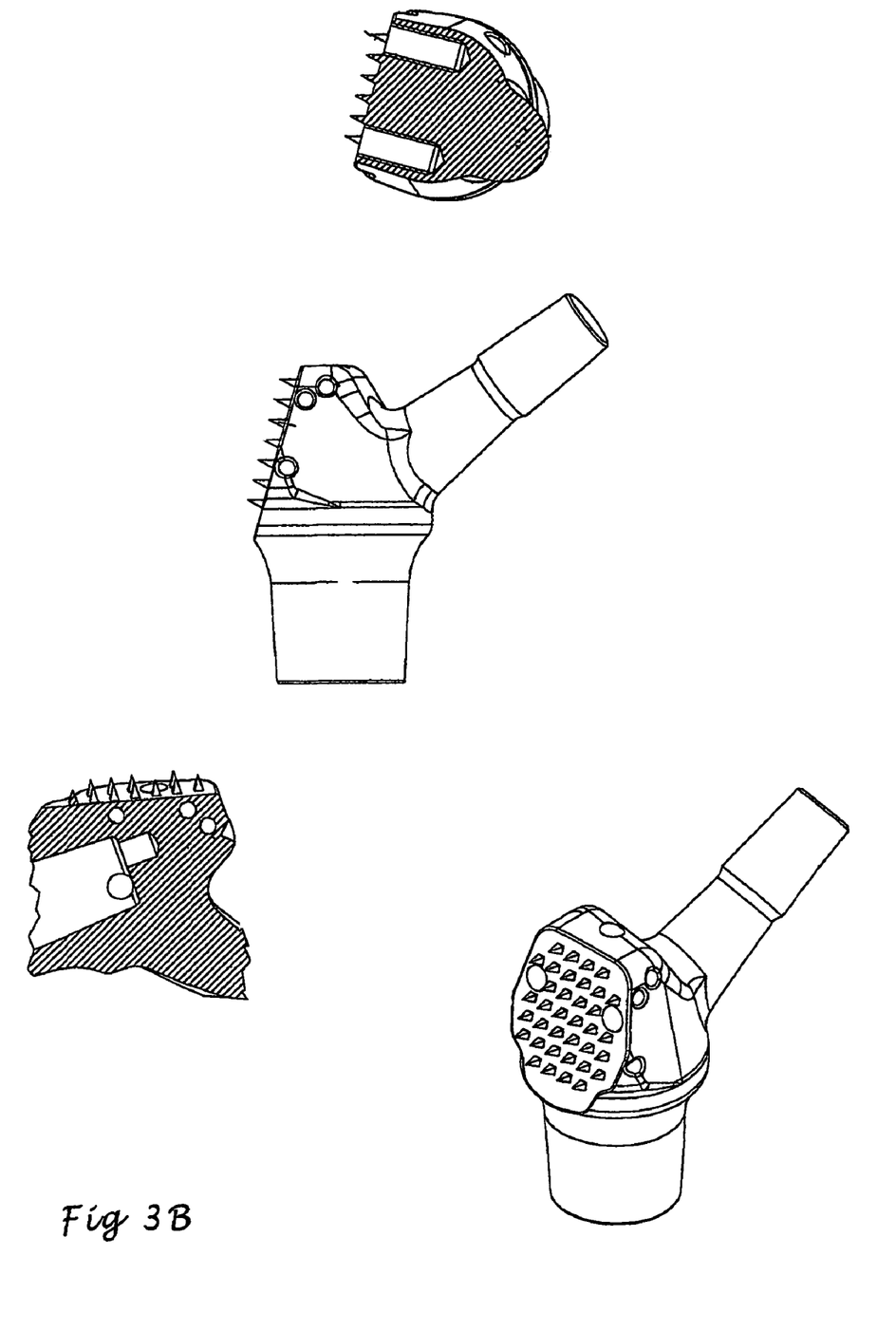
FIG. 3B shows various views of a trochanter replacement component in accordance with the invention.
Figure 4A:
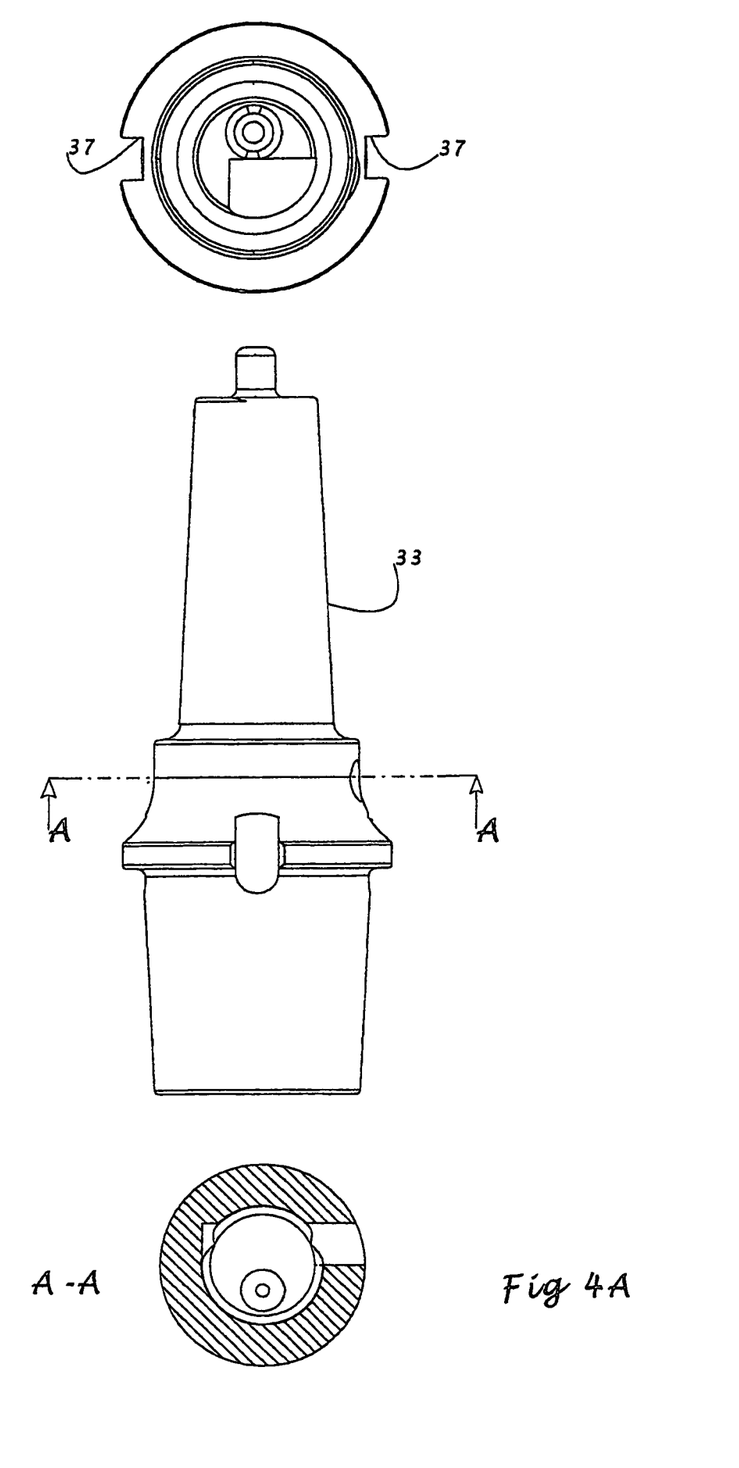
FIG. 4A shows various views of the modular shaft for use in the present invention.
Figure 4B:
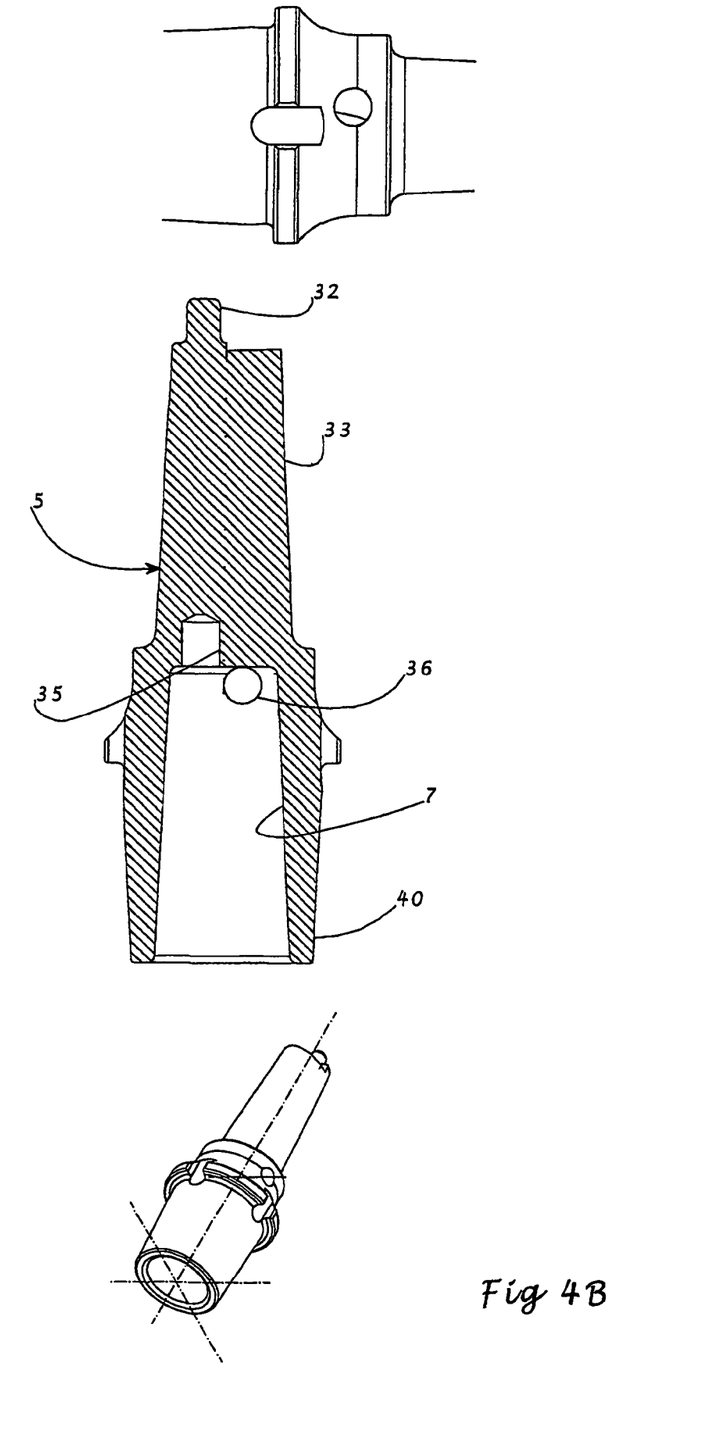
FIG. 4B shows various views of the modular shaft for use in the present invention.

Details of the trochanter component 1 are shown in the views of FIGS. 3A and 3B. It would be seen that the flat face 3 of the trochanter component 1 are formed in a pattern of spikes 30. This pattern of spikes is provided to ensure a firm connection with any residual bone 12 (see FIG. 1) and serves to further stabilize the prosthesis. It would be seen that the trochanter component has a female taper terminating internally with an offset recess 31. Recess 31 is shaped to be engaged with a projection 32 formed on the male taper 33 of the shaft 5. (See FIG. 4A). The trochanter component is provided with a transverse hole 34 into which a disassembly tool can be inserted to force the trochanter component and the shaft apart where disassembly is required. As can be seen in FIGS. 4A and 4B the shaft 5 also has a female taper 7 and is formed with a similar recess 35 to the recess 31 in the trochanter component. Shaft 5 also includes a transverse hole 36 into which a disassembly tool can be inserted to force apart the shaft and the stem component which is designed to fit into the taper 7.

Referring further to FIG. 3A it would be seen that the trochanter component also incorporates holes 44. These are intended for suturing the trochanter component to soft tissue such as tendons in the event that there is no residual bone, to which tendons are attached, which could be clamped to the stippled face 3.

The trochanter component is intended to be provided as a standard component of a modular system although there would be right and left handed versions. There may also be alternative trochanter components in which the degree of offset of the femoral neck differs to suit a particular patent.

As can be seen from FIGS. 4A and 4B the femoral shaft, although standardized so far as the tapers are concerned, is supplied in lengths of 15 mm intervals. The femoral shaft is also provided with notches 37 designed to engage with corresponding ears 38 which are integral with the collar 10. As can be seen from FIG. 6, collar 10 has an internal taper 39 adapted to fit on a corresponding taper 40 at one end of the shaft 5. The engagement of the collar on the shaft 5 and also the ears 38 in the notches 37 enables the collar to be fitted securely on the shaft. As can be seen from FIG. 6, the collar is supplied in a number of diameters, D1 and D2.

Figure 5:
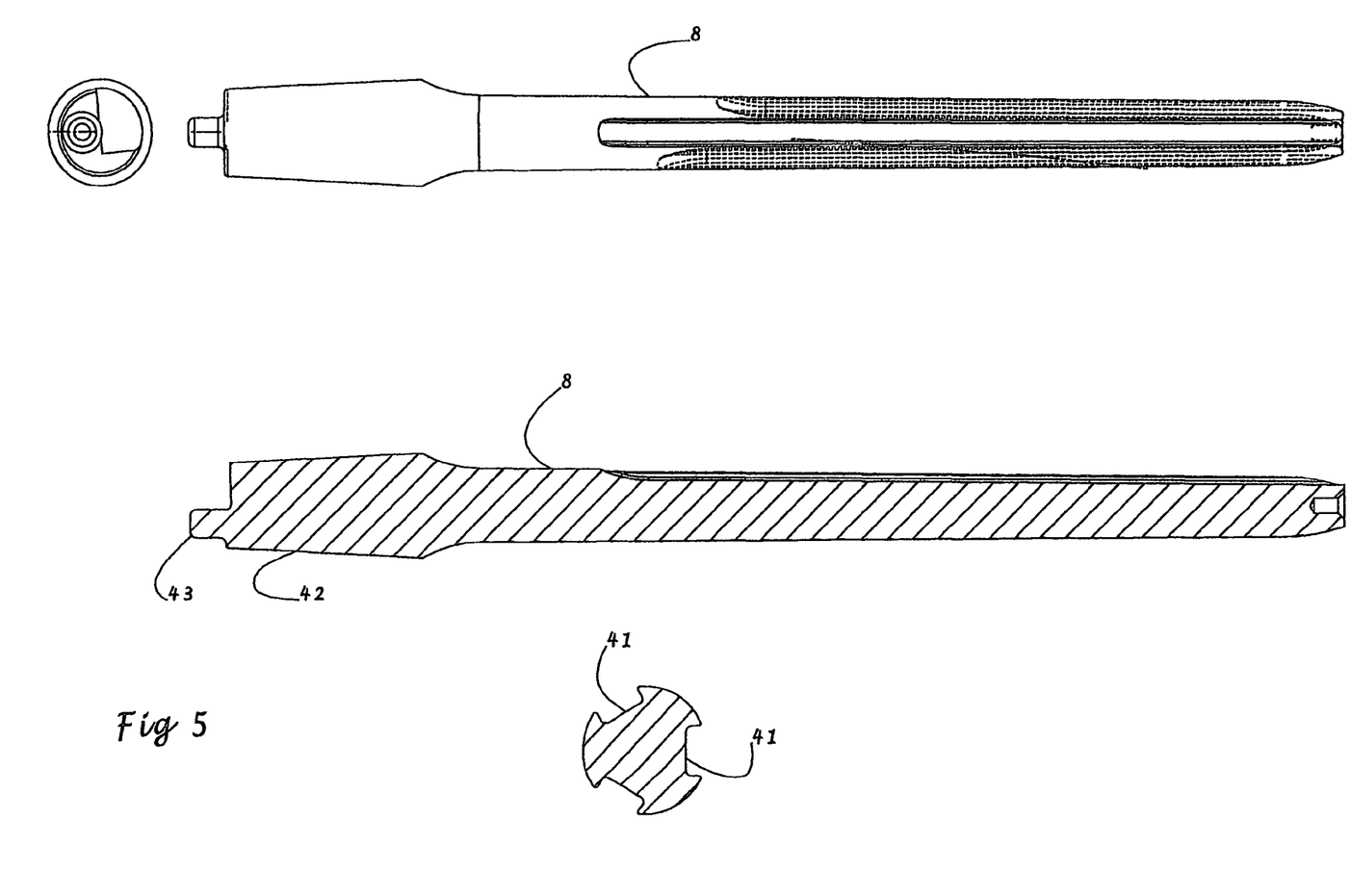
FIG. 5 shows various views of a femoral stem for use in the present invention.

FIG. 5 shows various views of the stem component 8. As can be seen from the cross-sectional view, the stem is formed with flutes for engaging in cortical bone and may be straight or curved to accommodate any curvature in the bone canal. The proximal end of the shaft has a taper 42 which corresponds with the internal taper 7 of the shaft component. The shaft also includes a projection 43 which corresponds with the recess 35 in the shaft component. The shaft component 5 includes a transverse hole 36 for disassembly purposes whereby a tool inserted through the hole will press apart the stem and the shaft by bearing on the corresponding end faces of the stem and shaft. As can be seen from FIG. 5, the stem is available in a number of diameters and lengths and may be curved or straight to accommodate the various surgical problems which might be encountered in fitting such a prosthesis.

Figure 7:
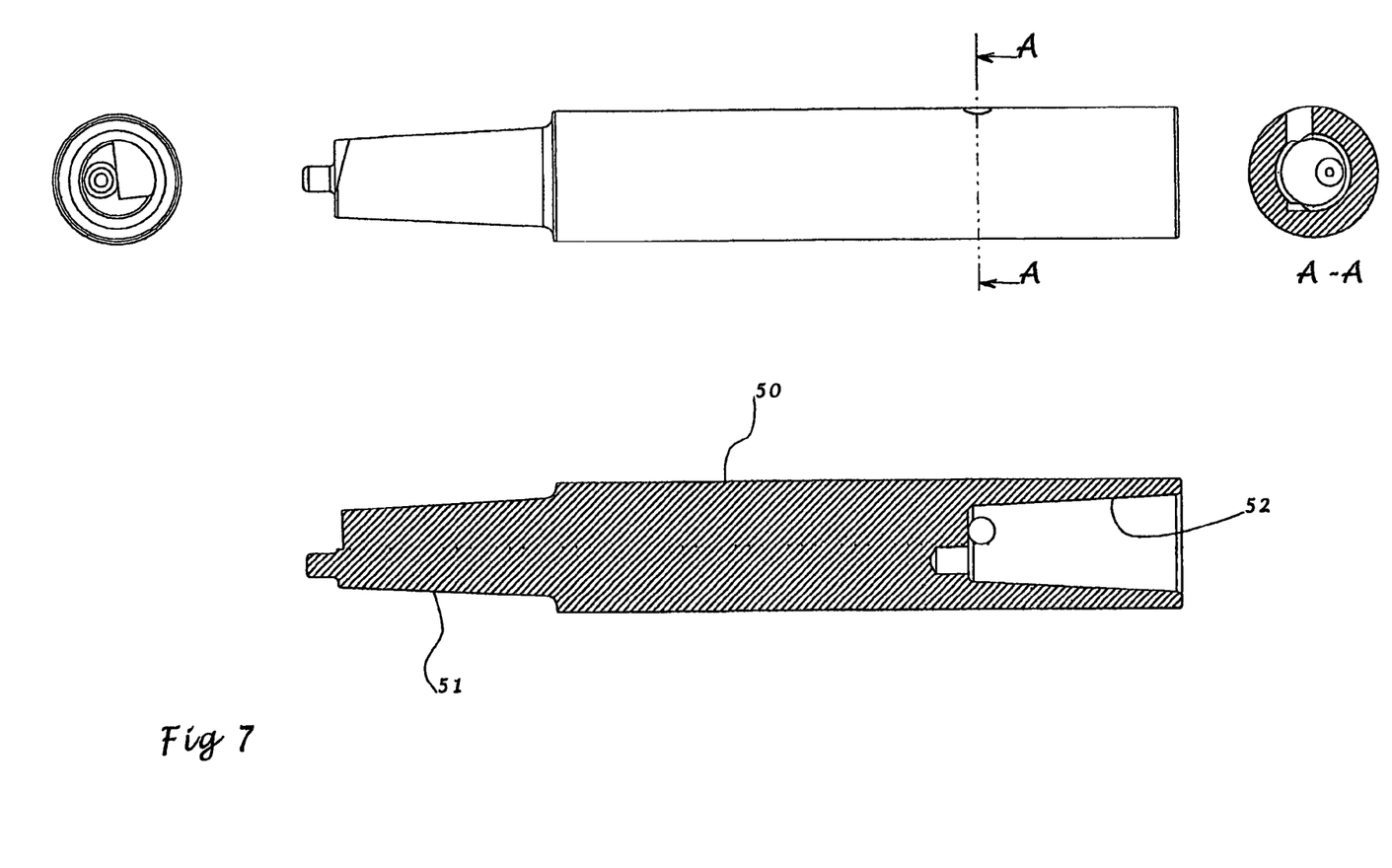

FIG. 7 shows a modular extension shaft which enables the total assemblies as shown in FIGS. 1 and 2 to be extended. Modular extension shaft 50 has male and female tapers, 51 and 52, respectively, at opposite ends which correspond respectively with taper 7 of the modular shaft and taper 42 of the modular stem. Of course, modular extension 50 may be used in conjunction with a standard shaft or alone to connect the trochanter component 1 or condular member 21 with the stem 8.

Although not shown in detail, the prosthesis shown in FIGS. 1 and 2 can be combined by omitting the shafts 8 and collars 10 to form a complete femoral replacement prosthesis. Also, analogously formed components could be employed to replace another long bone such as the humerus.

As described above, the components of the prosthesis can be readily dismantled by using a disassembly tool inserted in the transverse walls in the components at each tapered join either after a trial assembly or in a revision operation.

The material preferably used is a titanium alloy throughout except for the femoral heads where cobalt chromium or ceramic heads are preferably used.

The invention claimed is:

1. A prosthesis for partial and total replacement of a long bone in humans and animals, said prosthesis comprising:
    an end component having a longitudinal axis, an inwardly tapered primary recess having an open end, a secondary recess opening onto said primary recess which is offset from said longitudinal axis of said end component and a generally transversely extending cross-hole extending through said end component and having two open ends, one of said open ends of said cross-hole opening onto said primary recess for permitting access thereto by a disassembly tool,
    a shaft releasably coupled to said end component, said shaft having a longitudinal axis and a first and second end, wherein said first end of said shaft is outwardly tapered and is dimensioned and configured for receipt within said primary recess of said end component, and a projection formed on said first end extending generally longitudinally of said shaft but offset from said axis thereof which is dimensioned and configured for receipt with said secondary recess of said end component and wherein said second end of said shaft has an inwardly tapered primary recess having an open end, a secondary recess opening onto said primary recess which is offset from said longitudinal axis of said shaft and a generally transversely extending cross-hole extending through said shaft having two open ends, one of said open ends of said cross-hole opening onto said primary recess for permitting access thereto by a disassembly tool,
    and a stem releasably coupled to said shaft, said stem having a longitudinal axis and a first and second end, wherein said first end is intended for engagement in a resected bone having a resected face, and said second end is outwardly tapered and is dimensioned and configured for receipt with said primary recess of said second end of said shaft, and a projection formed on said second end extending generally longitudinally of said stem but offset from said axis thereof which is dimensioned and configured for receipt with said secondary recess of said second end of said shaft;
    and wherein said shaft, said stem, and said end component are releasably coupled together with said projections and secondary recesses being positioned so as to maintain said end component, said shaft and said stem in a desired angular relationship.

2. A prosthesis as claimed in claim 1, wherein a collar assembled to said shaft is dimensioned to abut said resected face of said bone into which said prosthesis is to be fitted, said collar having a portion adapted to taper towards said resected face and having a surface treatment designed to encourage bone growth over the tapered surface of said collar.

3. A prosthesis as claimed in claim 2, wherein said collar is formed with an externally stippled surface.

4. A prosthesis as claimed in claim 1, wherein said prosthesis is a proximal femoral replacement prosthesis, said prosthesis including a trochanter replacement component, assembled with one of said shaft and said stem.

5. A prosthesis as claimed in claim 4, wherein said trochanter replacement component is shaped to correspond approximately with an anatomical trochanter and includes a femoral neck for receiving a femoral ball and a generally flat face opposite said femoral neck for connection to residual bone.

6. A prosthesis as claimed in claim 5, wherein said generally flat face carries stipples for engagement with residual bone.

7. A prosthesis as claimed in claim 2 which is a proximal femoral replacement prosthesis, said prosthesis including a trochanter replacement component, assembled with one of said shaft and said stem.

8. A prosthesis as claimed in claim 3, wherein said prosthesis is a proximal femoral replacement prosthesis, said prosthesis including a trochanter replacement component, assembled with one of said shaft and said stem.

9. A prosthesis as claimed in claim 1, wherein said end component is a proximal end.

10. A prosthesis as claimed in claim 1, wherein said end component is a distal end.

11. A prosthesis as claimed in claim 2, wherein said collar is coated with hydroxyapatite.

12. A prosthesis as claimed in claim 2, wherein said collar is coated with bone growth promoting material.

13. A prosthesis as claimed in claim 4, wherein said trochanter replacement component is shaped to correspond approximately with an anatomical trochanter and includes a femoral neck for receiving a femoral ball and a generally flat face opposite said femoral neck for connection to soft tissue.

14. A prosthesis as claimed in claim 13, wherein said generally flat face carries stipples for engagement with residual bone.

* * * * *